(12) United States Patent
Bhongale et al.

(10) Patent No.: US 11,299,983 B2
(45) Date of Patent: Apr. 12, 2022

(54) DOWNHOLE GENERATION OF MICROWAVES FROM LIGHT

(71) Applicant: Halliburton Energy Services, Inc., Houston, TX (US)

(72) Inventors: Satyan Gopal Bhongale, Cypress, TX (US); Wolfgang Hartmut Nitsche, Humble, TX (US); Yenny Natali Martinez, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 407 days.

(21) Appl. No.: 16/305,537

(22) PCT Filed: Sep. 29, 2016

(86) PCT No.: PCT/US2016/054400
§ 371 (c)(1),
(2) Date: Nov. 29, 2018

(87) PCT Pub. No.: WO2018/063234
PCT Pub. Date: Apr. 5, 2018

(65) Prior Publication Data
US 2021/0231004 A1     Jul. 29, 2021

(51) Int. Cl.
*E21B 47/113* (2012.01)
*G02B 6/42* (2006.01)
(Continued)

(52) U.S. Cl.
CPC ........ *E21B 47/113* (2020.05); *G01N 33/2835* (2013.01); *G01V 3/30* (2013.01); *G02B 6/4292* (2013.01)

(58) Field of Classification Search
CPC .. E21B 47/113; E21B 49/08; E21B 2049/085; G01N 33/2835; G01V 3/30; G01V 8/24; G01V 8/005; G02B 6/4292
(Continued)

(56) References Cited

U.S. PATENT DOCUMENTS 6,243,508 B1   6/2001   Jewell et al.
6,355,928 B1   3/2002   Skinner et al.
(Continued)

OTHER PUBLICATIONS

International Search Report and The Written Opinion of the International Search Authority, or the Declaration, dated Jun. 8, 2017, PCT/US2016/054400, 9 pages, ISA/KR.

*Primary Examiner* — Alvaro E Fortich
*Assistant Examiner* — Zannatul Ferdous
(74) *Attorney, Agent, or Firm* — Haynes and Boone, LLP

(57) ABSTRACT

A method and system are disclosed that provide chemical composition data of a fluid. The system includes a first downhole electro-opto-mechanical device to transmit microwave radiation through the fluid. The microwave radiation is generated by the first downhole electro-opto-mechanical device in response to a first light signal. A second downhole electro-opto-mechanical device receives the microwave radiation and generates a second light signal in response to the received microwave radiation. A light detection device is coupled to the second downhole electro-opto-mechanical device to generate an electrical signal in response to the second light signal. The electrical signal is indicative of the chemical composition of the fluid.

20 Claims, 7 Drawing Sheets

(51) Int. Cl.
*G01V 3/30* (2006.01)
*G01N 33/28* (2006.01)

(58) Field of Classification Search
USPC .................................. 250/266, 269.1, 269.3
See application file for complete search history.

(56) References Cited

U.S. PATENT DOCUMENTS

| | | | |
|---|---|---|---|
| 2008/0319685 A1* | 12/2008 | Xie ......................... | G01F 1/712 |
| | | | 702/45 |
| 2010/0031754 A1* | 2/2010 | Atkinson ............. | G01N 1/2035 |
| | | | 73/861.04 |
| 2011/0150485 A1* | 6/2011 | Seidel ...................... | H03D 9/00 |
| | | | 398/115 |
| 2013/0119994 A1 | 5/2013 | Csutak | |
| 2015/0086152 A1* | 3/2015 | Samson .................... | G02F 1/29 |
| | | | 385/8 |
| 2016/0035962 A1* | 2/2016 | Yamashita ........... | H03H 9/1021 |
| | | | 310/348 |
| 2016/0252449 A1* | 9/2016 | Price ........................ | G01J 3/12 |
| | | | 356/364 |
| 2019/0226334 A1* | 7/2019 | Bhongale ................ | G01V 8/24 |

\* cited by examiner

DOWNHOLE GENERATION OF MICROWAVES FROM LIGHT

PRIORITY

The present application is a U.S. National Stage patent application of International Patent Application No. PCT/US2016/054400, filed on Sep. 29, 2016, the benefit of which is claimed and the disclosure of which is incorporated herein by reference in its entirety.

BACKGROUND

Microwaves may be used in a downhole environment for determining water cut measurements (i.e., ratio of water produced compared to total volume of liquid) as well as general chemical sensing measurements in the oil industry. However, conventional microwave generation devices tend to be bulky so that using them in the downhole environment is difficult. Microwave devices also are powered by electricity that may be difficult to provide within a borehole.

DETAILED DESCRIPTION

To address some of the challenges described above, as well as others, an electro-opto-mechanical device is used downhole to convert light photons into microwave photons (i.e., microwave radiation). The microwave radiation may then be used to perform downhole measurements of a fluid (e.g., water cut measurements) to determine the fluid's chemical composition. Another electro-opto-mechanical device receives the microwave radiation that is transmitted through the fluid and converts the received microwave radiation back to light photons for detection and analysis.

Figure 1:
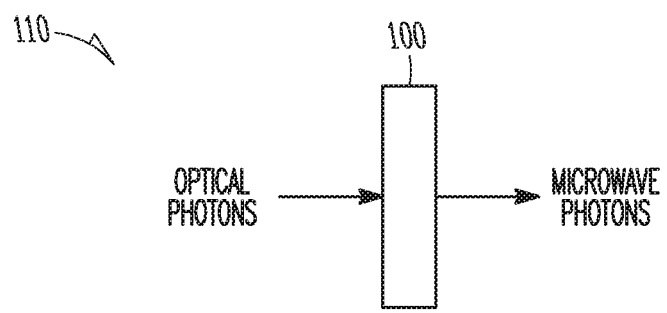
FIG. 1 is a diagram of an electro-opto-mechanical device, according to various embodiments.
Figure 1:
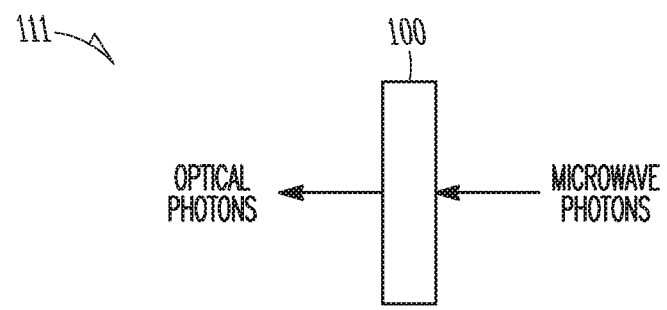

FIG. 1 is a diagram of an electro-opto-mechanical device 100, according to various embodiments. The electro-opto-mechanical device 100 may be any device that is able to produce microwave photons in response to optical photons and also produce optical photons in response to microwave photons.

There is no requirement that the optical photons represent visible light: any light that is appropriate to induce microwave photons (or vice versa) will work in the present embodiments. Furthermore, the light source can be of a single frequency (generating microwave radiation of a single frequency), or scanned over a range of frequencies that sufficiently meet resonance conditions such that spectroscopic measurements may be performed with the microwave radiation generated by the electro-opto-mechanical device 100. The reverse can also be true: the microwave radiation may be of a single frequency or scanned over a range of frequencies that sufficiently meet resonance conditions such that the light generated by the electro-opto-mechanical device is single frequency or exhibits a range of frequencies.

The electro-opto-mechanical device 100 is a resonant optical, microwave, and mechanical system which contains an opto-mechanical crystal such as an aluminum nitride (AlN) crystal, which may be piezoelectric. Other types of opto-mechanical crystals may be used in other embodiments.

The electro-opto-mechanical device 100 provides a nano-mechanical interface between optical photons and microwave electrical signals to achieve signal transfer between itinerant microwaves and optical fields by parametric electro-optical coupling using a localized phonon mode. The crystal may be monolithically integrated on an integrated circuit chip.

As an example of operation, the top FIG. 110 of FIG. 1 shows the electro-opto-mechanical device 100 that is receiving optical photons (i.e., light) from the left and producing microwave photons (e.g., microwave radiation) to the right. Such a scenario may be used in the downhole environment to transmit the microwave radiation through a fluid (e.g. liquid hydrocarbons, gas) for measurement of fluid chemical composition (e.g., water cut). Such an embodiment is shown in FIGS. 2 and 3 and described subsequently.

The bottom FIG. 111 of FIG. 1 shows an electro-opto-mechanical device 100 that is receiving microwave radiation from the right and producing optical photons to the left. Such a scenario may be used in the downhole environment to receive the microwave radiation that has been transmitted through the fluid and produce a light signal for analysis of the fluid's chemical composition.

In an embodiment, the electro-opto-mechanical devices 100 may be the same device used at different times to produce either microwave radiation or light. In another embodiment, two separate electro-opto-mechanical devices 100 are used.

Figure 2:
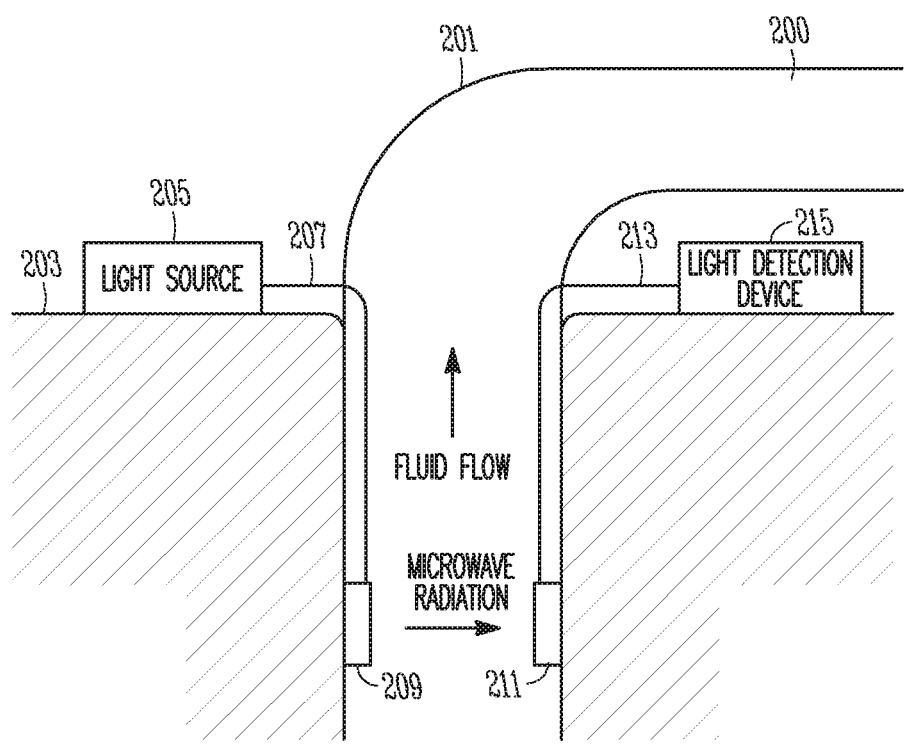
FIG. 2 is a diagram of a system incorporating the electro-opto-mechanical device of FIG. 1, according to various embodiments.
Figure 3:
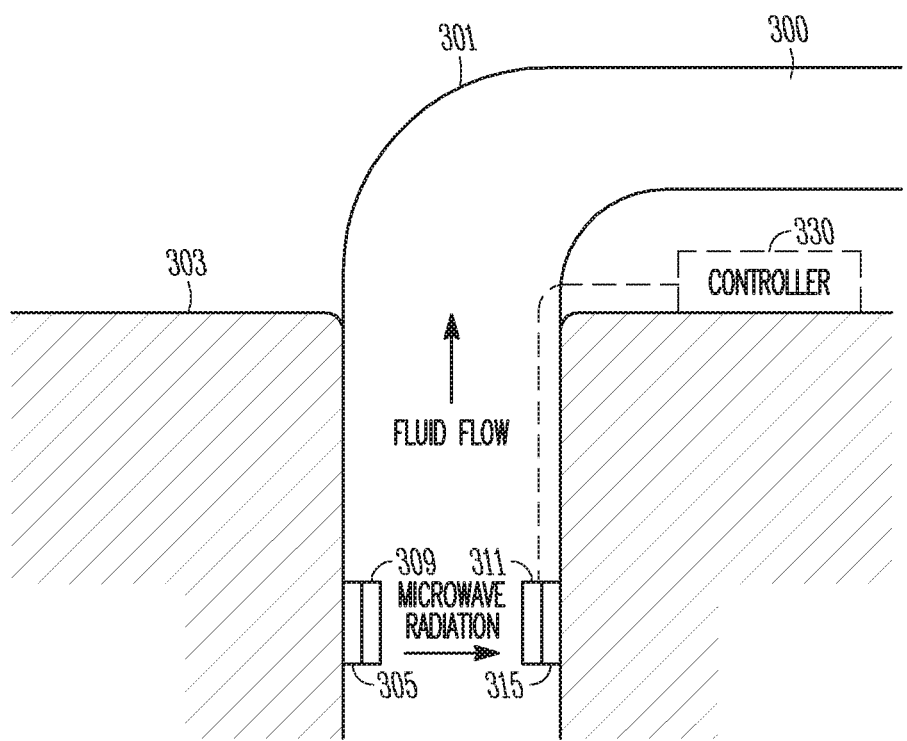
FIG. 3 is a diagram of another system incorporating the electro-opto-mechanical device of FIG. 1, according to various embodiments.

FIG. 2 is a diagram of a system incorporating the electro-opto-mechanical device of FIG. 1, according to various embodiments. This embodiment illustrates a pipe 201 having a fluid 200 flowing internal to the pipe. The fluid 200 may be liquid or gaseous hydrocarbons being pumped from a well.

A light source (e.g., laser) 205 may be located on the surface 203 of a geological formation and generates a first light signal that is transmitted through a fiber optic cable 207 that is coupled to a first electro-opto-mechanical device 209 (e.g., transmitter). The first electro-opto-mechanical device 209 acts as a transmitter to convert the light signal from the fiber optic cable 207 into microwave radiation that is transmitted through the fluid 200.

A second electro-opto-mechanical device 211 is located diametrically across the pipe 201 from the first electro-opto-mechanical device 209. The second electro-opto-mechanical device 211 (e.g., receiver) acts as a receiver to convert any received microwave radiation into a second light signal that is transmitted over a fiber optic cable 213 that is coupled to a light detection device 215 (e.g., photodiode) located on the surface 203.

In operation, a light signal is generated by the light source 205 and transmitted through the fiber optic cable 207 downhole to the transmitter electro-opto-mechanical device 209. The transmitter electro-opto-mechanical device 209 converts the light signal to microwave radiation that is transmitted through the fluid 200. The receiver electro-opto-mechanical device 211 receives the transmitted microwave radiation and converts the received microwave radiation to a light signal for transmission uphole through the fiber optic cable 213 to the light detection device 215. The light detection device 215 converts the received light signal to an electrical signal for analysis by a controller (shown in systems of FIGS. 5-7). In another embodiment, an optical coupler may be used to enable the receiver electro-opto-mechanical device 211 to use the same fiber optic cable 207 as that used by the transmitter electro-opto-mechanical device.

The electrical signal provides an indication of the fluid chemical composition properties of the fluid 200. For example, since water is typically more absorbent at certain microwave frequencies than other known components in the fluid, the electrical signal provides an indication of the attenuation of the received microwave radiation, as compared to the transmitted microwave radiation. The microwave radiation attenuation depends on the amount of water in the fluid; the greater the attenuation the more water is in the fluid (i.e., higher water cut). Other chemical properties may also be determined based on either the received light signal or the electrical signal. One method for determining the fluid chemical composition uses a form of spectroscopy that determines the level of attenuation created by the fluid between the source and receiver where the strength of attenuation depends on the frequency of the microwaves. Examples of such a method are discussed subsequently with reference to FIG. 4.

FIG. 3 is a diagram of another system incorporating the electro-opto-mechanical device of FIG. 1, according to various embodiments. This embodiment incorporates both the light source 305 and the light detection device 315 downhole instead of on the surface 303 as illustrated in FIG. 2.

They system of FIG. 3 operates in a pipe 301 having a flowing fluid 300. The light source 303 is coupled to the transmitter electro-opto-mechanical device 309 downhole. The light source 303 and the transmitter electro-opto-mechanical device 309 may be part of the same assembly or separate and coupled by a shorter fiber optic cable (not shown) than used in the embodiment of FIG. 2.

Similarly, the light detection device 315 is coupled to the receiver electro-opto-mechanical device 311 downhole. The light detection device 315 and the receiver electro-opto-mechanical device 311 may be part of the same assembly or separate and coupled by a shorter fiber optic cable (not shown) than used in the embodiment of FIG. 2.

Since the light detection device 315 converts the light signal from the receiver electro-opto-mechanical device 311 to an electrical signal, some mechanism is used to transfer a representation of the electrical signal to the surface 303 for analysis by a controller 330. For example, mud pulse telemetry may be used to transmit the representation of the electrical signal to the surface controller 330. In another embodiment, an electrical cable may connect the light detection device 315 to the controller 330 and transmit the electrical signal from the light detection device 315 to the controller 330.

For purposes of illustration only, the embodiments of FIGS. 2 and 3 show the diametric orientation for the transmitter and receiver such that the transmitter and receiver are located on opposite sides of the pipe. Other embodiments may locate the transmitter and receiver in an axial orientation such that one of either the transmitter or the receiver is located above or below the other. Still other embodiments may located one or more of the transmitter or receiver somewhere in the fluid flow away from the pipe sidewalls.

Figure 5:
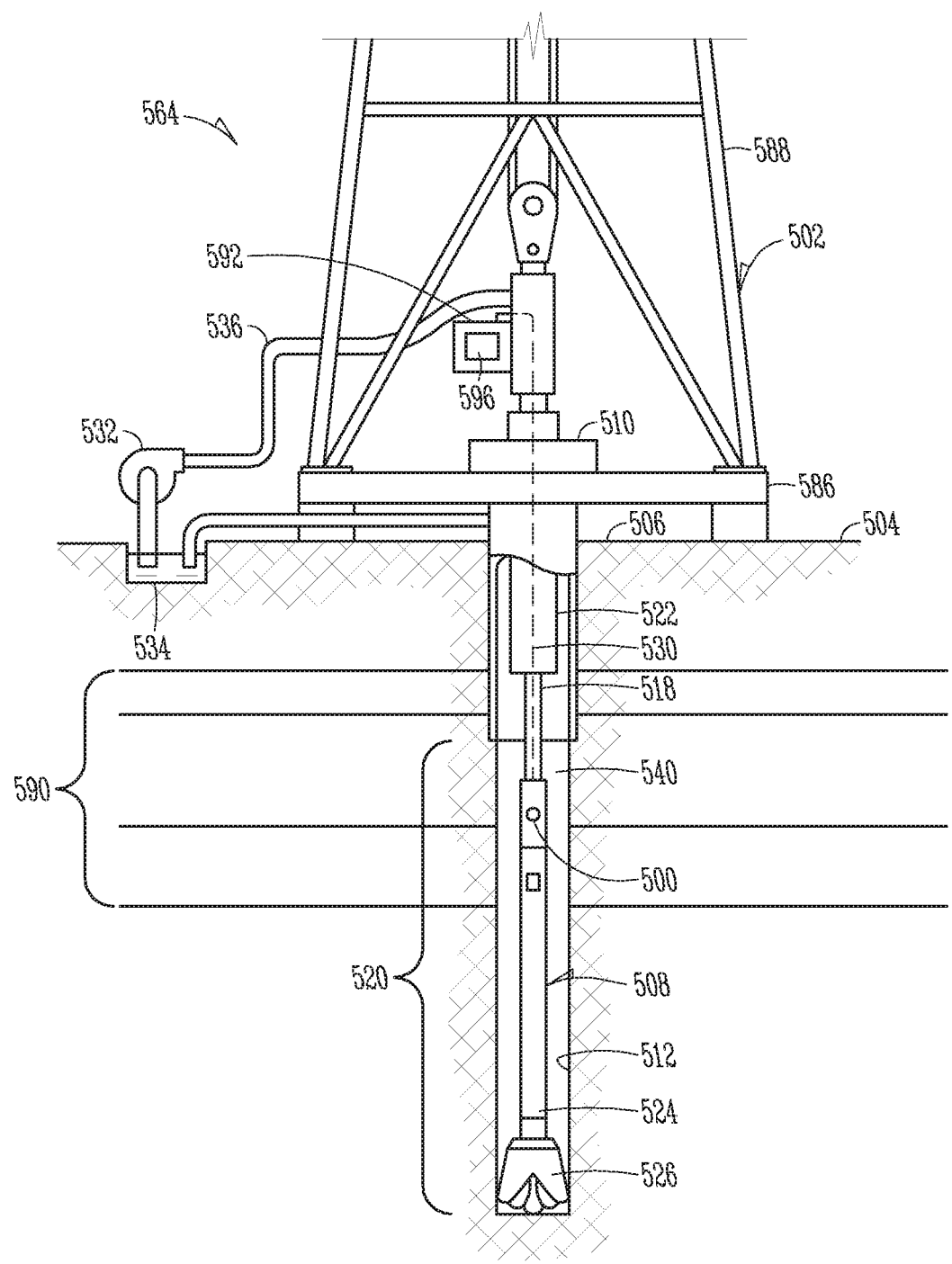
FIG. 5 is a diagram of a drilling system, according to various embodiments.
Figure 6:
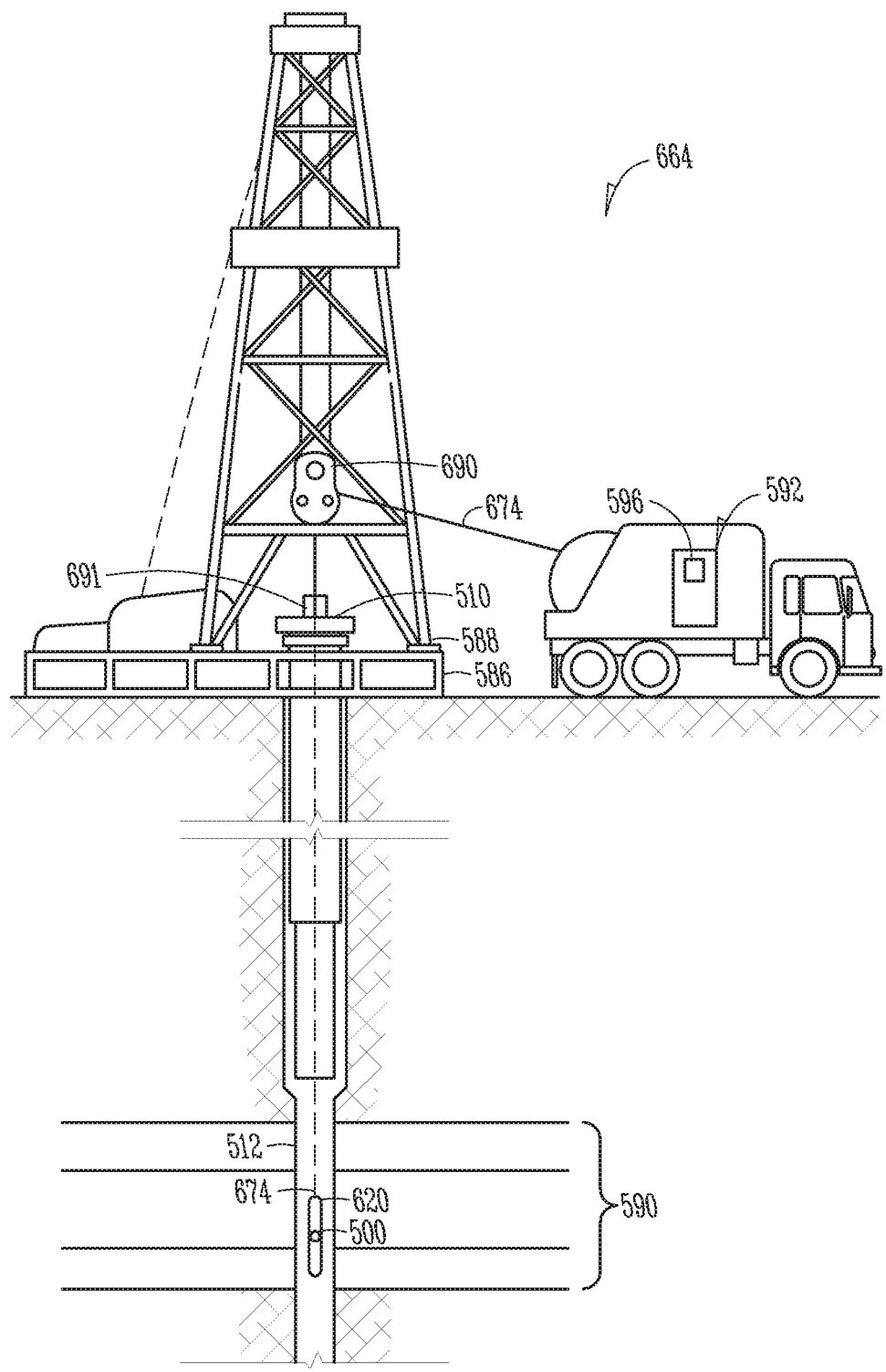
FIG. 6 is a diagram of a wireline system, according to various embodiments.

The embodiments of FIGS. 2 and 3 show only two scenarios for measurement of fluid chemical composition. Various combinations of these embodiments may also be used such as having the light source downhole and the light detection device on the surface or the light source on the surface with the light detection device downhole. Either of these embodiments would reduce the amount of fiber optic cable used as compared to the system of FIG. 2. FIGS. 5 and 6 show additional embodiments where the system may be used in either a drilling system or a wireline system.

Figure 4:
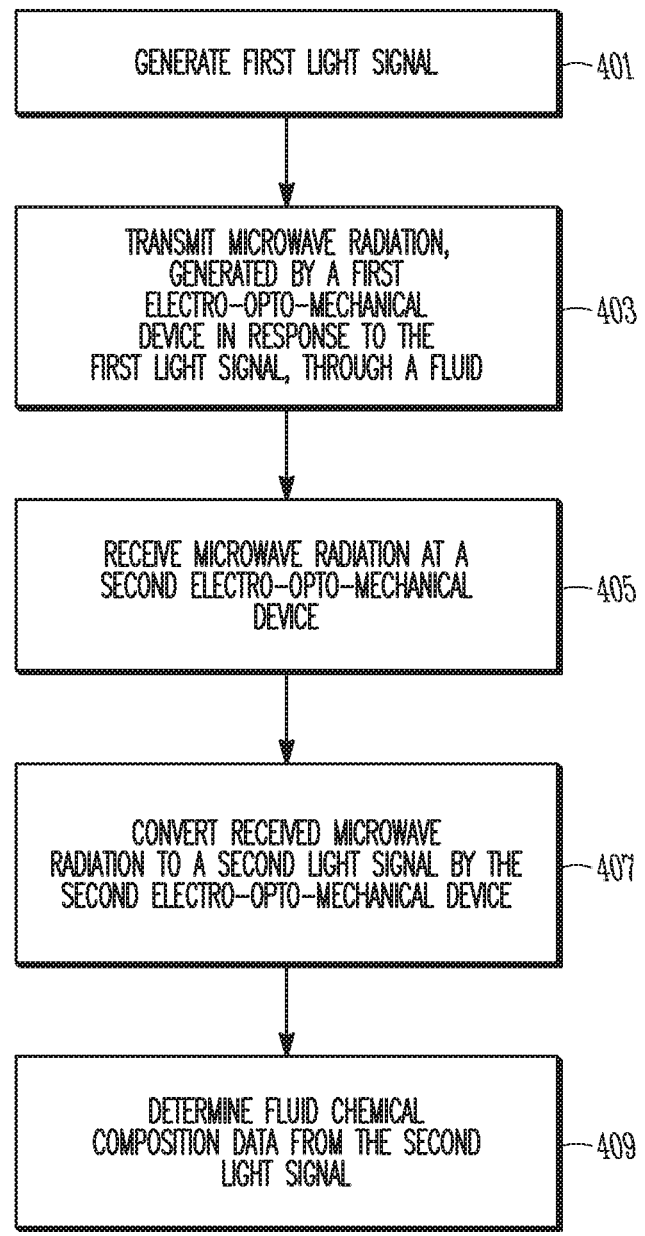
FIG. 4 is a flowchart of a method for downhole measurements with microwaves, according to various embodiments.

FIG. 4 is a flowchart of a method for downhole measurements with microwaves, according to various embodiments. In block 401 a first light signal is generated. In block 403, microwave radiation, generated by a first electro-opto-mechanical device in response to the first light signal, is transmitted through a fluid. In block 405, the microwave radiation is received by a second electro-opto-mechanical device. In block 407, the received microwave radiation is converted to a second light signal by the second electro-opto-mechanical device. In block 409, fluid chemical composition is determined from the second light signal.

The fluid chemical composition may be determined by converting the second light signal to an electrical signal and determining an attenuation of the received microwave radiation from the electrical signal. In an embodiment, the electrical signal may be transmitted uphole to a surface controller or the second light signal may be transmitted uphole to a surface light detection device through a second fiber optic cable. If the produced fluid (e.g., total fluid) comprises two different fluids, a single microwave frequency may be used to determine the composition of the total fluid. If the total fluid comprises multiple different fluids, measurements may be performed at multiple different frequencies since the attenuation of each respective fluid depends on the microwave frequency. Examples for determining the fluid composition in both of these scenarios is presented.

In the simplest example of the total fluid having only two different fluids, it is assumed that the first electro-opto-mechanical device (e.g., transmitter) is set a predetermined distance L (e.g., 10 centimeters (cm)) away from the second electro-opto-mechanical device (e.g., receiver). This means the microwave radiation travels through L=10 cm of the fluid to be sampled.

It is also assumed that water attenuates the microwave radiation by $\beta_{water}=1$ dB/cm, whereas oil attenuates it by $\beta_{oil}=0.5$ dB/cm. The amount of light (e.g., power) produced by the second electro-opto-mechanical device is approximately proportional to the power of the microwave radiation that hits the second electro-opto-mechanical device and, if a photo-detector is used to measure this light, the electric signal of the photo-detector is proportional to the light power.

Thus if $U_{measured}$ represents the electric signal from the photo-detector, and $U_0$ represents the electric signal that the photo-detector produces if there is no liquid in the beam-path through which the microwaves travel, then the water cut W may be calculated by:

$$W = \frac{10 \text{ dB} \log_{10}\left(\frac{U_0}{U_{measured}}\right) - L\beta_{oil}}{L\beta_{water} - L\beta_{oil}} = 2.0 \log_{10}\left(\frac{U_0}{U_{measured}}\right) - 1.0$$

where the water cut W is defined as the volume of the produced water $W_{water}$ to the total produced volume $V_{total}$. If it is assumed that the total fluid is a mixture of water and oil only, then the total volume is $V_{total}=V_{water}+V_{oil}$ and the water cut is represented by:

$$W = \frac{V_{water}}{V_{total}} = \frac{V_{water}}{V_{water} + V_{oil}}$$

The numbers given in this example are for purposes of illustration only since other values may be used in other examples. Additionally, instead of determining the water-cut W, other chemical substances may be identified in a substantially similar way.

In the example of determining multiple different fluids in the total fluid, the fraction of each individual fluid in the total fluid may be determined if measurements at multiple different microwave frequencies are performed. This is the case because the attenuation of each individual fluid depends in a unique way on the microwave frequency.

To determine the composition of the total fluid that may contain up to N different liquids, measurements using N–1 different microwave frequencies are performed. If more than N–1 measurements are made, the reliability of the data increases.

Assuming N different fluids are present in the total fluid, the absorption (having units of dB/cm) at frequency $f_m$ is:

$$\alpha_{total}(f_m) = \sum_{n=1}^{N} \frac{V_n}{V_{total}} \alpha_n(f_m)$$

where $\alpha_n(f_m)$ represents the absorption of the $n^{th}$ fluid at frequency $f_m$ and $$\frac{V_n}{V_{total}}$$

represents the fraction of the $n^{th}$ fluid.

Since N is the total number of fluids that might be present, it is known that:

$$V_{total} = \sum_{n=1}^{N} V_n.$$

This measurement can be performed at many different frequencies of $f_m$ such as $f_m = f_1, f_2, \ldots, M$ where the $\alpha_{total}(f_m)$ is determined for each measurement. The values of $\alpha_n(f_m)$ are known in advance since these can be determined in the lab. Provided that M≥N–1, numerical fitting can be used to determine the $$\frac{V_n}{V_{total}}$$

for each of the fluids and, thereby, determine the composition of the total fluid.

In subsequently described system embodiments of FIGS. 5 and 6, one of either the transmitter or the receiver electro-opto-mechanical devices may be located in a tool housing while the other electro-opto-mechanical device may be located on the borehole wall. In another embodiment, both the transmitter and receiver electro-opto-mechanical devices are located in the tool housing and a passage in the housing enables fluid to enter the tool housing in order for measurements to be accomplished as described previously when the fluid flows between the transmitter and receiver electro-opto-mechanical devices.

FIG. 5 is a diagram showing a drilling system, according to various embodiments. The system 564 includes a drilling rig 502 located at the surface 504 of a well 506. The drilling rig 502 may provide support for a drillstring 508. The drillstring 508 may operate to penetrate the rotary table 510 for drilling the borehole 512 through the subsurface formations 590. The drillstring 508 may include a drill pipe 518 and the bottom hole assembly (BHA) 520 (e.g., drill string), perhaps located at the lower portion of the drill pipe 518.

The BHA 520 may include drill collars 522, a downhole tool 524, stabilizers, sensors, an RSS, a drill bit 526, as well as other possible components. The drill bit 526 may operate to create the borehole 512 by penetrating the surface 504 and the subsurface formations 590. The BHA 520 may further include a downhole tool housing including the transmitter and/or receiver electro-opto-mechanical devices 500 to acquire downhole fluid chemical composition data for processing, as described previously. As described previously, one or both of the light source or the light detection device may also be included in the downhole tool or on the surface.

During drilling operations within the borehole 512, the drillstring 508 (perhaps including the drill pipe 518 and the BHA 520) may be rotated by the rotary table 510. Although not shown, in addition to or alternatively, the BHA 520 may also be rotated by a motor (e.g., a mud motor) that is located downhole. The drill collars 522 may be used to add weight to the drill bit 526. The drill collars 522 may also operate to stiffen the BHA 520, allowing the BHA 520 to transfer the added weight to the drill bit 526, and in turn, to assist the drill bit 526 in penetrating the surface 504 and subsurface formations 590.

During drilling operations, a mud pump 532 may pump drilling fluid (sometimes known by those of ordinary skill in the art as "drilling mud") from a mud pit 534 through a hose 536 into the drill pipe 518 and down to the drill bit 526. The drilling fluid can flow out from the drill bit 526 and be returned to the surface 504 through an annular area 540 between the drill pipe 518 and the sides of the borehole 512. The drilling fluid may then be returned to the mud pit 534, where such fluid is filtered. In some examples, the drilling fluid can be used to cool the drill bit 526, as well as to provide lubrication for the drill bit 526 during drilling operations. Additionally, the drilling fluid may be used to remove subsurface formation cuttings created by operating the drill bit 526.

A workstation 592 including a controller 596 may include modules comprising hardware circuitry, a processor, and/or memory circuits that may store software program modules and objects, and/or firmware, and combinations thereof that are configured to execute at least the method of FIG. 4. The workstation 592 may also include modulators and demodulators for modulating and demodulating a light signal transmitted downhole through a fiber optic cable 530 or telemetry received through the fiber optic cable 530 from the downhole environment. The workstation 592 and controller 596 are shown near the rig 502 only for purposes of illustration as these components may be located at remote locations.

These implementations can include a machine-readable storage device having machine-executable instructions, such as a computer-readable storage device having computer-executable instructions. Further, a computer-readable storage device may be a physical device that stores data represented by a physical structure within the device. Such a physical device is a non-transitory device. Examples of a non-transitory computer-readable storage medium can include, but not be limited to, read only memory (ROM), random access memory (RAM), a magnetic disk storage device, an optical storage device, a flash memory, and other electronic, magnetic, and/or optical memory devices.

FIG. 6 is a diagram showing a wireline system 664, according to various examples of the disclosure. The system 664 may comprise at least one wireline logging tool body 620, as part of a wireline logging operation in a borehole 512, including the transmitter and/or receiver electro-opto-mechanical devices 500 described previously.

A drilling platform 586 equipped with a derrick 588 that supports a hoist 690 can be seen. Drilling oil and gas wells is commonly carried out using a string of drill pipes connected together so as to form a drillstring that is lowered through a rotary table 510 into the borehole 512. Here it is assumed that the drillstring has been temporarily removed from the borehole 512 to allow the wireline logging tool body 620, such as a probe or sonde with the transmitter and/or receiver electro-opto-mechanical devices 500, to be lowered by wireline or logging cable 674 (e.g., slickline cable) into the borehole 512. Typically, the wireline logging tool body 620 is lowered to the bottom of the region of interest and subsequently pulled upward at a substantially constant speed.

During the upward trip, at a series of depths, the tool with the transmitter and/or receiver electro-opto-mechanical devices 500 may be used to generate microwave radiation from light and measure fluid chemical composition using the microwave radiation. The resulting fluid chemical composition may be communicated to a surface logging facility (e.g., workstation 592) for processing, analysis, and/or storage. The workstation 592 may have a controller 596 that is able to execute any methods disclosed herein and to operate as part of a downhole microwave generation from light system.

Figure 7:
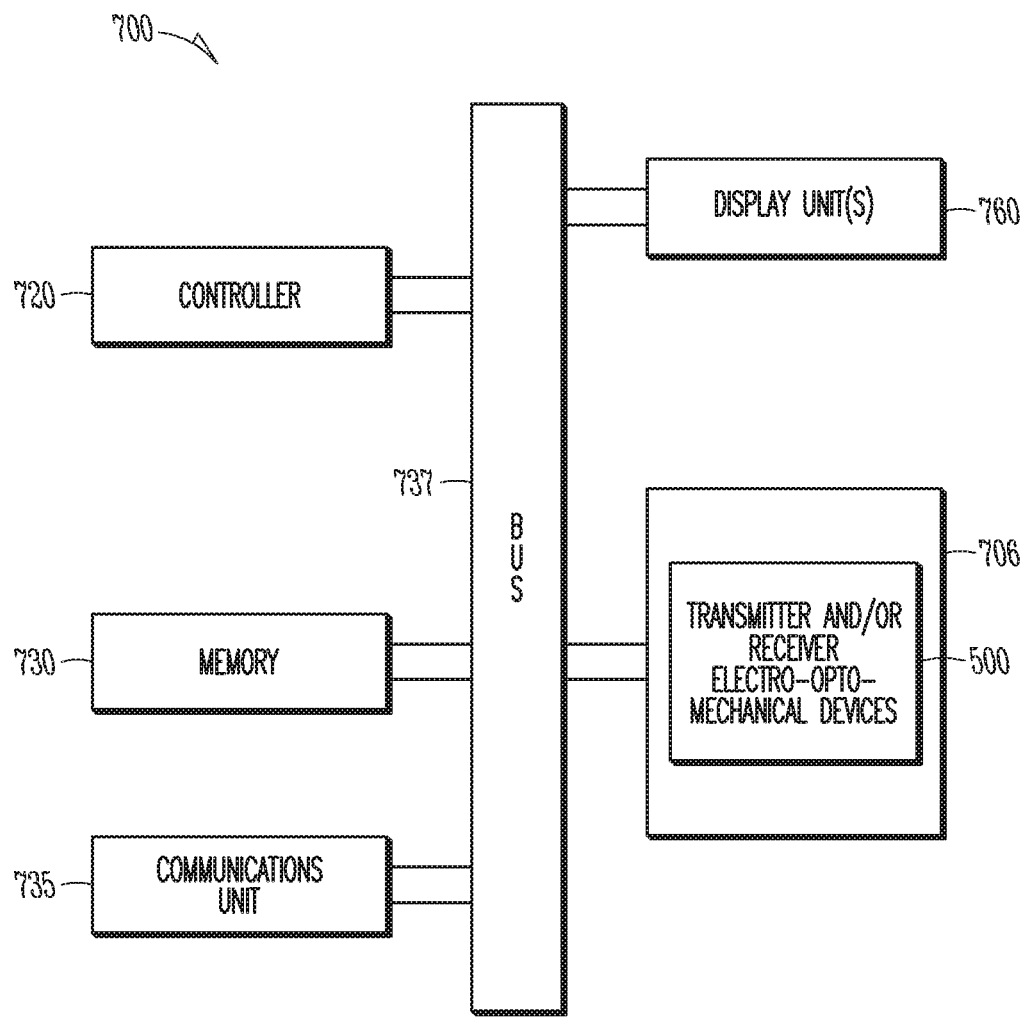
FIG. 7 is a block diagram of an example system operable to implement the activities of multiple methods, according to various embodiments.

FIG. 7 is a block diagram of an example system 700 operable to implement the activities of multiple methods, according to various examples of the disclosure. The system 700 may include a tool housing 706 having the transmitter and/or receiver electro-opto-mechanical devices 500 disposed therein. The system 700 may be implemented as shown in FIGS. 5 and 6 with reference to the workstation 592 and controller 596.

The system 700 may include a controller 720, a memory 730, and a communications unit 735. The memory 730 may be structured to include a database. The controller 720, the memory 730, and the communications unit 735 may be arranged to operate as a processing unit to control operation of the transmitter and/or receiver electro-opto-mechanical devices 500 and execute any methods disclosed herein in order to determine the fluid chemical composition.

The communications unit 735 may include communications capability for communicating from downhole to the surface or from the surface to downhole. Such communications capability can include a telemetry system such as mud pulse telemetry. In another example, the communications unit 735 may use combinations of wired communication technologies and wireless technologies.

The system 700 may also include a bus 737 that provides electrical conductivity among the components of the system 700. The bus 737 can include an address bus, a data bus, and a control bus, each independently configured or in an integrated format. The bus 737 may be realized using a number of different communication mediums that allows for the distribution of components of the system 700. The bus 737 may include a network. Use of the bus 737 may be regulated by the controller 720.

The system 700 may include display unit(s) 760 as a distributed component on the surface of a wellbore, which may be used with instructions stored in the memory 730 to implement a user interface to monitor the operation of the tool 706 or components distributed within the system 700. The user interface may be used to input parameter values for thresholds such that the system 700 can operate autonomously substantially without user intervention in a variety of applications. The user interface may also provide for manual override and change of control of the system 700 to a user. Such a user interface may be operated in conjunction with the communications unit 735 and the bus 737.

These implementations can include a machine-readable storage device having machine-executable instructions, such as a computer-readable storage device having computer-executable instructions. Further, a computer-readable storage device may be a physical device that stores data represented by a physical structure within the device. Such a physical device is a non-transitory device. Examples of machine-readable storage devices can include, but are not limited to, read only memory (ROM), random access memory (RAM), a magnetic disk storage device, an optical storage device, a flash memory, and other electronic, magnetic, and/or optical memory devices.

Many embodiments may be realized. Several examples will now be described.

Example 1 is a method comprising: generating a first light signal; transmitting microwave radiation, generated by a first electro-opto-mechanical device in response to the first light signal, through a fluid; receiving the microwave radiation; converting the received microwave radiation to a second light signal with a second electro-opto-mechanical device; and determining a fluid chemical composition based on the second light signal.

In Example 2, the subject matter of Example 1 optionally includes wherein determining the fluid chemical composition comprises: converting the second light signal to an electrical signal; and determining an attenuation of the received microwave radiation from the electrical signal.

In Example 3, the subject matter of Example 2 optionally includes transmitting the electrical signal uphole to a surface controller.

In Example 4, the subject matter of any one or more of Examples 1-3 optionally include wherein determining the fluid chemical composition comprises determining an attenuation of the received microwave radiation.

In Example 5, the subject matter of Example 4 optionally includes wherein determining the fluid chemical composition comprises determining a water cut of the fluid.

In Example 6, the subject matter of Example 5 optionally includes wherein the attenuation of the received microwave increases with the water cut of the fluid.

In Example 7, the subject matter of any one or more of Examples 1-6 optionally include transmitting the first light signal downhole to the first electro-opto-mechanical device through a first fiber optic cable.

In Example 8, the subject matter of Example 7 optionally includes transmitting the second light signal uphole to a surface light detection device through a second fiber optic cable.

Example 9 is a system comprising: a first downhole electro-opto-mechanical device configured to transmit microwave radiation through a fluid, wherein the microwave radiation is generated by the first downhole electro-opto-mechanical device in response to a first light signal; a second downhole electro-opto-mechanical device configured to receive the microwave radiation and generate a second light signal in response to the received microwave radiation; and a light detection device coupled to the second downhole electro-opto-mechanical device and configured to generate an electrical signal in response to the second light signal, wherein the electrical signal is indicative of a chemical composition of the fluid.

In Example 10, the subject matter of Example 9 optionally includes a light source coupled to the first downhole electro-opto-mechanical device to generate the first light signal.

In Example 11, the subject matter of Example 10 optionally includes a fiber optic cable that couples the first downhole electro-opto-mechanical device to the light source.

In Example 12, the subject matter of any one or more of Examples 10-11 optionally include wherein the light source is located downhole with the first downhole electro-opto-mechanical device or on a surface of a geological formation.

In Example 13, the subject matter of any one or more of Examples 9-12 optionally include wherein the light detection device is located on a surface of a geological formation.

In Example 14, the subject matter of Example 13 optionally includes wherein the light detection device is coupled to the second downhole electro-opto-mechanical device with a fiber optic cable.

In Example 15, the subject matter of any one or more of Examples 9-14 optionally include a controller coupled to the light detection device to determine the chemical composition of the fluid in response to the electrical signal.

In Example 16, the subject matter of any one or more of Examples 9-15 optionally include wherein the first and second electro-opto-mechanical devices are piezoelectric opto-mechanical crystals.

In Example 17, the subject matter of Example 16 optionally includes wherein the piezoelectric opto-mechanical crystals are aluminum nitride crystals.

Example 18 is a system comprising: a tool housing comprising: at least one of a transmitter electro-opto-mechanical device or a receiver electro-opto-mechanical device, wherein the transmitter electro-opto-mechanical device is configured to generate microwave radiation in response to a first light signal and transmit the microwave radiation through a fluid and the receiver electro-opto-mechanical device is configured to receive the microwave radiation and generate a second light signal in response to the microwave radiation; and a controller coupled to the tool housing and configured to determine a chemical composition of the fluid in response to the second light signal.

In Example 19, the subject matter of Example 18 optionally includes wherein the transmitter electro-opto-mechanical device and the receiver electro-opto-mechanical device are both located in the tool housing and the tool housing further comprises a passage in the tool housing configured to allow the fluid into the tool housing.

In Example 20, the subject matter of Example 19 optionally includes wherein the tool housing further comprises: a light source coupled to the first electro-opto-mechanical device for generating the first light signal; and a light detection device coupled to the second electro-opto-mechanical device for generating an electrical signal in response to the second light signal.

This disclosure is intended to cover any and all adaptations or variations of various embodiments. Combinations of the above embodiments, and other embodiments not specifically described herein, will be apparent to those of skill in the art upon reviewing the above description.

In this description, references to "one embodiment" or "an embodiment," or to "one example" or "an example" in this description are not intended necessarily to refer to the same embodiment or example; however, neither are such embodiments mutually exclusive, unless so stated or as will be readily apparent to those of ordinary skill in the art having the benefit of this disclosure. Thus, a variety of combinations and/or integrations of the embodiments and examples described herein may be included, as well as further embodiments and examples as defined within the scope of all claims based on this disclosure, as well as all legal equivalents of such claims.

As used herein, "downhole" (together with its derivatives) refers to axial movement or a relative axial location closer to the bottom of the borehole and away from the surface. Conversely, "uphole" (together with its derivatives) refers to axial movement or a relative axial location closer to the surface and away from the bottom of the borehole.

In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separate embodiment.

What is claimed is:

1. A method comprising:
   generating a first light signal comprised of optical photons;
   converting, by a first electro-opto-mechanical device, the optical photons into microwave radiation comprised of microwave photons;
   transmitting the microwave radiation through a fluid;
   receiving the microwave radiation;
   converting the received microwave radiation to a second light signal comprised of optical photons with a second electro-opto-mechanical device; and
   determining a fluid chemical composition based on the second light signal.

2. The method of claim 1, wherein determining the fluid chemical composition comprises:
   converting the second light signal to an electrical signal; and
   determining an attenuation of the received microwave radiation from the electrical signal.

3. The method of claim 2, further comprising transmitting the electrical signal uphole to a surface controller.

4. The method of claim 1, wherein determining the fluid chemical composition comprises determining an attenuation of the received microwave radiation.

5. The method of claim 4, wherein determining the fluid chemical composition comprises determining a water cut of the fluid.

6. The method of claim 5, wherein the attenuation of the received microwave increases with the water cut of the fluid.

7. The method of claim 1, further comprising transmitting the first light signal downhole to the first electro-opto-mechanical device through a first fiber optic cable.

8. The method of claim 7, further comprising transmitting the second light signal uphole to a surface light detection device through a second fiber optic cable.

9. A system comprising:
a first downhole electro-opto-mechanical device configured to transmit microwave radiation through a fluid, wherein the first downhole electro-opto-mechanical device, in response to receipt of a first light signal comprised of optical photons, converts the optical photons into microwave radiation comprised of microwave photons;
a second downhole electro-opto-mechanical device configured to receive the microwave radiation and convert the microwave photons into a second light signal comprised of optical photons in response to the received microwave radiation; and
a light detection device coupled to the second downhole electro-opto-mechanical device and configured to generate an electrical signal in response to the second light signal, wherein the electrical signal is indicative of a chemical composition of the fluid.

10. The system of claim 9, further comprising a light source coupled to the first downhole electro-opto-mechanical device to generate the first light signal.

11. The system of claim 10, further comprising a fiber optic cable that couples the first downhole electro-opto-mechanical device to the light source.

12. The system of claim 10, wherein the light source is located downhole with the first downhole electro-opto-mechanical device or on a surface of a geological formation.

13. The system of claim 9, wherein the light detection device is located on a surface of a geological formation.

14. The system of claim 13, wherein the light detection device is coupled to the second downhole electro-opto-mechanical device with a fiber optic cable.

15. The system of claim 9, further comprising a controller coupled to the light detection device to determine the chemical composition of the fluid in response to the electrical signal.

16. The system of claim 9, wherein the first and second electro-opto-mechanical devices are piezoelectric opto-mechanical crystals.

17. The system of claim 16, wherein the piezoelectric opto-mechanical crystals are aluminum nitride crystals.

18. A system comprising:
a tool housing comprising:
at least one of a transmitter electro-opto-mechanical device or a receiver electro-opto-mechanical device, wherein the transmitter electro-opto-mechanical device is configured to, in response to receipt of a first light signal comprised of optical photons, convert the optical photons into microwave radiation comprised of microwave photons and transmit the microwave radiation through a fluid and the receiver electro-opto-mechanical device is configured to receive the microwave radiation and convert the microwave photons into a second light signal comprised of optical photons in response to the microwave radiation; and
a controller coupled to the tool housing and configured to determine a chemical composition of the fluid in response to the second light signal.

19. The system of claim 18, wherein the transmitter electro-opto-mechanical device and the receiver electro-opto-mechanical device are both located in the tool housing and the tool housing further comprises a passage in the tool housing configured to allow the fluid into the tool housing.

20. The system of claim 19, wherein the tool housing further comprises:
a light source coupled to the first electro-opto-mechanical device for generating the first light signal; and
a light detection device coupled to the second electro-opto-mechanical device for generating an electrical signal in response to the second light signal.

\* \* \* \* \*